US009273353B2

(12) United States Patent
Gambini et al.

(10) Patent No.: US 9,273,353 B2
(45) Date of Patent: *Mar. 1, 2016

(54) INSTRUMENT FOR MONITORING POLYMERASE CHAIN REACTION OF DNA

(71) Applicant: LIFE TECHNOLOGIES CORPORATION, Carlsbad, CA (US)

(72) Inventors: Michael R. Gambini, W. Barnstable, MA (US); John G. Atwood, West Redding, CT (US); Anthony L. Cerrone, Northford, CT (US); Edward J. Lakatos, Bethel, CT (US); Eugene F. Young, Marietta, GA (US)

(73) Assignee: Life Technologies Corporation, Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/730,989

(22) Filed: Jun. 4, 2015

(65) Prior Publication Data

US 2015/0322488 A1 Nov. 12, 2015

Related U.S. Application Data

(63) Continuation of application No. 11/804,151, filed on May 17, 2007, which is a continuation of application (Continued)

(51) Int. Cl.
*C12M 1/34* (2006.01)
*C12M 3/00* (2006.01)
(Continued)

(52) U.S. Cl.
CPC . *C12Q 1/686* (2013.01); *B01L 7/52* (2013.01); *G01N 21/274* (2013.01);
(Continued)

(58) Field of Classification Search
CPC ............ C12Q 1/686; C12Q 1/04; B01L 7/52; B01L 2200/10; B01L 2300/0654; B01L 2300/0663; B01L 2300/1811; B01L 2300/0636; G01N 21/6428; G01N 21/6439; G01N 21/6452; G01N 21/253; G01N 33/54366; G01N 33/54373; C12M 1/3446; B01J 2219/00722; B01J 2219/00659; B01J 19/0046; C40B 40/00; B82Y 30/00
See application file for complete search history.

(56) References Cited

U.S. PATENT DOCUMENTS

| 4,076,420 A | 2/1978 | De Maeyer et al. |
| 4,200,801 A | 4/1980 | Schuresko |

(Continued)

FOREIGN PATENT DOCUMENTS

| DE | 37 17 274 | 1/1988 |
| DE | 19651667 | 9/1997 |

(Continued)

OTHER PUBLICATIONS 08011345.9, *Extended European Search Report dated* Aug. 27, 2008, 2 pgs.

(Continued)

*Primary Examiner* — Michael Hobbs

(57) ABSTRACT

An optical instrument monitors PCR replication of DNA in a reaction apparatus having a temperature cycled block with vials of reaction ingredients including dye that fluoresces in presence of double-stranded DNA. A beam splitter passes an excitation beam to the vials to fluoresce the dye. An emission beam from the dye is passed by the beam splitter to a CCD detector from which a processor computes DNA concentration. A reference strip with a plurality of reference emitters emit reference beams of different intensity, from which the processor selects an optimum emitter for compensating for drift. Exposure time is automatically adjusted for keeping within optimum dynamic ranges of the CCD and processor. A module of the beam splitter and associated optical filters is associated with selected dye, and is replaceable for different dyes.

27 Claims, 7 Drawing Sheets

Related U.S. Application Data

No. 11/333,483, filed on Jan. 17, 2006, now Pat. No. 8,557,566, which is a continuation of application No. 10/216,620, filed on Aug. 9, 2002, now Pat. No. 7,008,789, which is a continuation of application No. 09/700,536, filed as application No. PCT/US99/11088 on May 17, 1999, now Pat. No. 6,818,437.

(60) Provisional application No. 60/092,784, filed on Jul. 14, 1998, provisional application No. 60/085,765, filed on May 16, 1998.

(51) Int. Cl.
 *C12Q 1/68* (2006.01)
 *B01L 7/00* (2006.01)
 *G01N 21/27* (2006.01)
 *G01N 21/64* (2006.01)
 *B01L 3/00* (2006.01)

(52) U.S. Cl.
 CPC ......... *G01N 21/645* (2013.01); *G01N 21/6428* (2013.01); *G01N 21/6452* (2013.01); *B01L 3/5085* (2013.01); *B01L 2200/10* (2013.01); *B01L 2300/0654* (2013.01); *B01L 2300/0663* (2013.01); *B01L 2300/1811* (2013.01); *C12Q 2545/101* (2013.01); *G01N 2021/6419* (2013.01); *G01N 2021/6421* (2013.01); *G01N 2021/6439* (2013.01); *G01N 2021/6441* (2013.01); *G01N 2021/6463* (2013.01); *G01N 2021/6482* (2013.01); *G01N 2201/0245* (2013.01); *G01N 2201/0628* (2013.01); *G01N 2201/0635* (2013.01)

(56) References Cited

U.S. PATENT DOCUMENTS

| | | |
|---|---|---|
| 4,284,897 A | 8/1981 | Sawamura et al. |
| 4,412,543 A | 11/1983 | Vassiliadis et al. |
| 4,487,477 A | 12/1984 | Helms et al. |
| 4,626,684 A | 12/1986 | Landa |
| 4,643,877 A | 2/1987 | Opitz |
| 4,660,971 A | 4/1987 | Sage et al. |
| 4,661,913 A | 4/1987 | Wu |
| 4,673,289 A | 6/1987 | Gaucher |
| 4,683,202 A | 7/1987 | Mullis |
| 4,756,427 A | 7/1988 | Gohde |
| 4,786,165 A | 11/1988 | Yamamoto et al. |
| 4,832,815 A | 5/1989 | Kambara et al. |
| 4,887,721 A | 12/1989 | Martin et al. |
| 4,972,258 A | 11/1990 | Wolf et al. |
| 4,989,977 A | 2/1991 | North |
| 5,018,866 A | 5/1991 | Osten |
| 5,030,002 A | 7/1991 | North, Jr. |
| 5,073,029 A | 12/1991 | Eberly et al. |
| 5,091,652 A | 2/1992 | Mathies et al. |
| 5,127,730 A | 7/1992 | Brelje et al. |
| 5,141,609 A | 8/1992 | Sweedler et al. |
| 5,169,601 A | 12/1992 | Ohta et al. |
| 5,173,748 A | 12/1992 | Bilhorn |
| 5,192,412 A | 3/1993 | Kambara |
| 5,215,883 A | 6/1993 | Chu |
| 5,241,363 A | 8/1993 | Garner |
| 5,243,540 A | 9/1993 | Van Albert et al. |
| 5,256,880 A | 10/1993 | Loree et al. |
| 5,268,080 A | 12/1993 | Kambara et al. |
| 5,275,951 A | 1/1994 | Chow et al. |
| 5,277,780 A | 1/1994 | Kambara |
| 5,304,810 A | 4/1994 | Amos |
| 5,314,602 A | 5/1994 | Kambara et al. |
| 5,315,375 A | 5/1994 | Allen |
| 5,355,215 A | 10/1994 | Schroeder et al. |
| 5,366,608 A | 11/1994 | Kambara |
| 5,371,016 A | 12/1994 | Berndt |
| 5,371,624 A | 12/1994 | Nagano et al. |
| 5,377,004 A | 12/1994 | Owen et al. |
| 5,383,023 A | 1/1995 | Walleczek |
| 5,389,544 A | 2/1995 | Sugata et al. |
| 5,439,578 A | 8/1995 | Dovichi et al. |
| 5,470,710 A | 11/1995 | Weiss et al. |
| 5,475,610 A | 12/1995 | Atwood et al. |
| 5,491,343 A | 2/1996 | Brooker |
| 5,515,169 A | 5/1996 | Cargill et al. |
| 5,527,684 A | 6/1996 | Mabile |
| 5,529,679 A | 6/1996 | Takahashi et al. |
| 5,547,849 A | 8/1996 | Baer et al. |
| 5,567,947 A | 10/1996 | Kebabian |
| 5,582,705 A | 12/1996 | Yeung et al. |
| 5,585,242 A | 12/1996 | Bouma et al. |
| 5,595,708 A | 1/1997 | Berndt |
| 5,627,643 A | 5/1997 | Birnbaum et al. |
| 5,633,752 A | 5/1997 | Tsuchiya et al. |
| 5,635,402 A | 6/1997 | Alfano |
| 5,636,017 A | 6/1997 | Bruno et al. |
| 5,656,493 A | 8/1997 | Mullis et al. |
| 5,667,656 A | 9/1997 | Kambara |
| 5,672,880 A | 9/1997 | Kain |
| 5,675,155 A | 10/1997 | Pentoney, Jr. et al. |
| 5,695,626 A | 12/1997 | Yeung et al. |
| 5,710,628 A | 1/1998 | Waterhouse et al. |
| 5,717,602 A | 2/1998 | Kenning |
| 5,730,850 A | 3/1998 | Kambara et al. |
| 5,736,333 A | 4/1998 | Livak et al. |
| 5,741,411 A | 4/1998 | Yeung et al. |
| 5,741,412 A | 4/1998 | Dovichi et al. |
| 5,754,291 A | 5/1998 | Kain |
| 5,759,781 A | 6/1998 | Ward et al. |
| 5,766,889 A | 6/1998 | Atwood |
| 5,779,978 A | 7/1998 | Hartmann et al. |
| 5,784,157 A | 7/1998 | Gorfinkel et al. |
| 5,790,727 A | 8/1998 | Dhadwal et al. |
| 5,792,610 A | 8/1998 | Witney et al. |
| 5,822,060 A | 10/1998 | Linowski et al. |
| 5,833,826 A | 11/1998 | Nordman |
| 5,833,827 A | 11/1998 | Anazawa et al. |
| 5,834,203 A | 11/1998 | Katzir et al. |
| 5,837,196 A | 11/1998 | Pinkel et al. |
| 5,846,842 A | 12/1998 | Herron et al. |
| 5,854,684 A | 12/1998 | Stabile et al. |
| 5,858,653 A | 1/1999 | Duran et al. |
| 5,863,502 A | 1/1999 | Southgate |
| 5,872,623 A | 2/1999 | Stabile et al. |
| 5,926,271 A | 7/1999 | Couderc et al. |
| 5,928,907 A | 7/1999 | Woudenberg et al. |
| 5,943,129 A | 8/1999 | Hoyt et al. |
| 5,958,349 A | 9/1999 | Petersen et al. |
| 6,005,663 A | 12/1999 | Waterhouse et al. |
| 6,017,434 A | 1/2000 | Simpson et al. |
| 6,040,940 A | 3/2000 | Kawasaki |
| 6,057,114 A | 5/2000 | Akong et al. |
| 6,066,459 A | 5/2000 | Garini et al. |
| 6,084,667 A | 7/2000 | Melman et al. |
| 6,096,272 A | 8/2000 | Clark et al. |
| 6,110,683 A | 8/2000 | Reynolds et al. |
| 6,133,986 A | 10/2000 | Johnson |
| 6,140,048 A | 10/2000 | Müller et al. |
| 6,197,575 B1 | 3/2001 | Griffith et al. |
| 6,249,341 B1 | 6/2001 | Basiji et al. |
| 6,252,717 B1 | 6/2001 | Grosskopf |
| 6,256,148 B1 | 7/2001 | Gasworth |
| 6,271,972 B1 | 8/2001 | Kedar et al. |
| 6,287,871 B1 | 9/2001 | Herron et al. |
| 6,309,601 B1 | 10/2001 | Juncosa et al. |
| 6,331,438 B1 | 12/2001 | Aylott et al. |
| 6,331,441 B1 | 12/2001 | Balch |
| 6,337,740 B1 | 1/2002 | Parce |
| 6,352,672 B1 | 3/2002 | Mabile |
| 6,355,934 B1 | 3/2002 | Osgood et al. |
| 6,364,516 B1 | 4/2002 | Li et al. |
| 6,381,025 B1 | 4/2002 | Bornhop et al. |
| 6,388,788 B1 | 5/2002 | Harris |
| 6,411,835 B1 | 6/2002 | Modell et al. |

(56) References Cited

U.S. PATENT DOCUMENTS

| | | |
|---|---|---|
| 6,455,861 B1 | 9/2002 | Hoyt |
| 6,464,852 B1 | 10/2002 | Gorfinkel et al. |
| 6,485,625 B1 | 11/2002 | Simpson et al. |
| 6,524,860 B1 | 2/2003 | Seidel et al. |
| 6,529,275 B2 | 3/2003 | Amirkhanian et al. |
| 6,542,241 B1 | 4/2003 | Thorwirth et al. |
| 6,686,582 B1 | 2/2004 | Volcker et al. |
| 6,717,668 B2 | 4/2004 | Treado |
| 6,746,864 B1 | 6/2004 | McNeil et al. |
| 6,749,735 B1 | 6/2004 | Le Febre |
| 6,800,452 B1 | 10/2004 | McNeil et al. |
| 6,818,437 B1 | 11/2004 | Gambini et al. |
| 6,856,390 B2 | 2/2005 | Nordman et al. |
| 7,008,789 B2 | 3/2006 | Gambini et al. |
| 7,030,371 B2 | 4/2006 | Vasic et al. |
| 7,183,103 B2 | 2/2007 | Gambini et al. |
| 7,265,833 B2 | 9/2007 | Oldham et al. |
| 7,387,891 B2 * | 6/2008 | Boege ............... B01L 7/52 250/459.1 |
| 7,468,793 B2 | 12/2008 | Nordman et al. |
| 7,498,164 B2 | 3/2009 | Oldham et al. |
| 8,361,785 B2 * | 1/2013 | Oldham ............... B01L 7/52 250/459.1 |
| 8,492,138 B2 * | 7/2013 | Boege ............... B01L 7/52 250/459.1 |
| 8,557,566 B2 * | 10/2013 | Gambini ............... B01L 7/52 435/286.1 |
| 2001/0033374 A1 | 10/2001 | Hoyt |
| 2002/0055178 A1 | 5/2002 | Wardiaw |
| 2002/0060791 A1 | 5/2002 | Stumbo et al. |
| 2002/0146688 A1 | 10/2002 | Kinjo |
| 2004/0070763 A1 | 4/2004 | Yeung et al. |
| 2004/0165256 A1 | 8/2004 | Teng et al. |

FOREIGN PATENT DOCUMENTS

| | | |
|---|---|---|
| DE | 19649605 | 6/1998 |
| DE | 19748211 | 5/1999 |
| EP | 0065409 | 11/1982 |
| EP | 0640828 | 3/1995 |
| EP | 0668498 | 8/1995 |
| EP | 0686699 | 12/1995 |
| EP | 0616211 | 1/1999 |
| EP | 0987539 | 3/2000 |
| JP | 57186169 | 11/1982 |
| JP | 60108457 | 6/1985 |
| JP | 62016911 A | 1/1987 |
| JP | 62016911 U | 1/1987 |
| JP | 62-169911 A | 7/1987 |
| JP | 63287177 | 11/1988 |
| JP | 3-504046 | 6/1990 |
| JP | 6216911 | 8/1994 |
| JP | 07120392 | 5/1995 |
| JP | 07120393 | 5/1995 |
| JP | 7-163397 A | 6/1995 |
| JP | 07174701 | 7/1995 |
| JP | 8066199 | 3/1996 |
| JP | 8094940 | 4/1996 |
| JP | 09072843 | 3/1997 |
| JP | 09166752 | 6/1997 |
| JP | 2009-230246 | 9/1997 |
| JP | 09281078 | 10/1997 |
| JP | 09292572 | 11/1997 |
| JP | 10-096862 | 4/1998 |
| JP | 10115781 | 5/1998 |
| JP | 10115783 A | 5/1998 |
| JP | 2009072843 | 4/2009 |
| WO | WO-95/11961 | 5/1995 |
| WO | WO-95/23348 | 8/1995 |
| WO | WO-95/30139 | 11/1995 |
| WO | WO96/05488 | 2/1996 |
| WO | WO-9607888 | 3/1996 |
| WO | WO-97/19342 | 5/1997 |
| WO | WO-97/21089 | 6/1997 |
| WO | WO-9723649 | 7/1997 |
| WO | WO-97/34171 | 9/1997 |
| WO | WO-97/39330 | 10/1997 |
| WO | WO-97/46708 | 12/1997 |
| WO | WO-9746707 | 12/1997 |
| WO | WO-9807022 | 2/1998 |
| WO | WO-98/12536 | 3/1998 |
| WO | WO-98/13683 | 4/1998 |
| WO | WO-99/50916 | 10/1999 |
| WO | WO-99/60381 | 11/1999 |
| WO | WO-00/25113 | 5/2000 |
| WO | WO01/35079 | 5/2001 |
| WO | WO-02/17219 | 2/2002 |
| WO | WO-02/23163 | 3/2002 |
| WO | WO-02/059577 | 8/2002 |
| WO | WO-03/010524 | 2/2003 |

OTHER PUBLICATIONS

U.S. Appl. No. 09/351,660, "Automatic Masking of Objects in Images", Jul. 13, 1999, 42 pgs.

Altria, Kevin, "Capillary electrophoresis", *Royal Society of Chemistry*, 7 sheets, 2000.

Brochure, "Charge-Coupled Devices for Quantitative Electronic Imaging", *Photometrics, Ltd.*, 1992, 1-3, 6-17.

Bronstein, Irena et al., "Chemiluminescent and Bioluminescent reporter gene assays", *Analytical Biochemistry*, vol. 219, 1994, 169-181.

EP 10012503, "Partial Search Report mailed May 23, 2012", 7 Pgs.

EP10012503, "Extended European Search Report", 23 Pgs.

Genome Sequencing Center, Washington University School of , "EST & GSS Projects", http://www.genome.wustl.edu/est/est_general/trace_intro.html, St. Louis, MO, Monday, Mar. 26, 2001.

H W Sands Corporation, "OLED Emitters Selected by Color Emission", http://www,hwsands.com/productlists/oled/oled_emitters_color_emission.htm, Jan. 10, 2003, 5 pgs.

Hacman, D. et al., "Jahrbuch fur Optik und Feinmechnik", 1980, 65-83.

Hebner, T. R. et al., "Local Tuning of Organic Light-Emitting Diode Color by Dye Droplet Application American Institute of Physics.", *Applied Physics, Letters* 73, 1998, 1775-1777.

Higuchi, R. et al., "Kinetic PCR Analysis: Real-Time Monitoring of DNA Amplification Reactions", *BioTechnology*, vol. 11, Sep. 1993, 1026-1030.

Hoy, Terry, "Cell Sorting: Principles", http://www.uwcm.ac.uk/study/medicine/haematology/cytonetuk/documents/sort.pps, Printed Apr. 14, 2004, 2004.

Karger, et al., "Multiwavelength Fluorescence Detection for DNA Sequencing Using Capillary Electrophoresis", *Nucleic Acids Res.* 19, 1991, 4955-4962.

Kinjo, Masataka et al., "Ultrasensitive hybridization analysis using fluorescence correlation spectroscopy", *Nucleic Acids Research*, vol. 23, No. 10, May 25, 1995, pp. 1795-1799.

Kostichka, Anthony J. et al., "High Speed Automated DNA Sequencing in Ultrathin Slab Gels", *Nature Biotechnology*, vol. 10, Jan. 1992, 78-81.

Kricka, Larry J. , "Nonisotopic DNA Probe Techniques", *Academic Press*, 1992, 7 pages.

Manoir, S. D. et al., "Hardware and Software Requirements for Quantitative Analysis of Comparative Genomic Hybridization", 1995, 6 pgs.

Miyamoto, *Journal of the Optical Society of America*, vol. 51, No. 1, 1961, 17-20.

Mullikin, et al., "(Proc. SPIE, 1994, vol. 2173, p. 1-12)".

Novotny, Milos, "Capillary electrophoresis", *Current Opinion in Biotechnology*, vol. 7, 1996, 29-34.

PCT/US99/011088, International Search Report mailed Sep. 15, 1999, 3 pgs.

Qiu, et al., "Room Temperature Ultraviolet Emission From an Organic Light-Emitting Diode", *American Institute of Physics*, Jul. 25, 2001, 2276-2278.

Reel, Richard , "Camera Lens Spectrograph Optics Design for MegaGUT", Jan. 16, 1997, 1-42.

(56) References Cited

OTHER PUBLICATIONS

Ririe, et al., "Product Differentiation by Analysis of DNA Melting Curves During the Polymerase Chain Reaction", *Analytical Biochemistry*, vol. 245, 1997, 154-160.

Rosemount Analytical, "Model 890 UV SO2 Analyzer", *Instruction Manual*, 1998, 82 Pgs.

Ross, et al., "High Sensitivity is Key to CE Detection Boost", *Today's Chemist at Work*, vol. 6(8), Sep. 1997, 31-36.

Sanger, F. et al., "DNA sequencing with chain-terminating inhibitors", *Proc. Natl. Acad. Sci. USA*, vol. 74(12), 1977, 5463-5467.

Simpson, et al., "A Transmission Imaging Spectrograph and Microfabricated Channel System for DNA Analysis", *Electrophoresis*, vol. 21, 2000, 135-149.

Smith, Lloyd et al., "Fluorescence detection in automated DNA sequence analysis", *Nature*, vol. 321, 1986, 674-679.

Smith, Lloyd, "The Future of DNA Sequencing", *Science*, vol. 262, 1993, 530-532.

Smith, Warren, "The Design of Optical Systems", *Modern Optical Engineering*, 2nd Edition, Section 9.1-9.7, 1990, 235-265.

Sweedler, J et al., "Fluorescence Detection in Capillary zone electrophoresis using a charge-coupled device with time-delayed intergration.", *Analytical chemistry, American chemical society Columbus*, US, vol. 63, No. 5, XP000207134 ISSN: 0003-2700, Mar. 1, 1991, 496-502.

Taylor, et al., "Fluorescence Microscopy of Living Cells in Culture", *Methods in Cell Biology*, Part B, 1989, 1-27, 38-45, and 379-388.

Teresko, "Winning Technologies: Organic Light Emitting Diode", *Industry Week*, Dec. 11, 2000, 3 pgs.

The *New Encyclopedia Britannica*, vol. 13, 15th Edition, 1982, 613.

The Brockhaus Enzyklopadie, 1. Aufl., 7, Band, 1988, 439.

Tollefsrud, "Organic Light Emitting Diode", http://komar.cs.stthornas.edulqm425/01sITollefsrud2.htm, Tollefsrud, Electronic Paper, Jan. 10, 2003, 5 pgs.

Volcker, Martin et al., "MikroskOfgestotzte Fluoreszenz-Photonen-Korrelation", *Technisches Messen*, vol. 63, Apr. 1, 1996, 128-135.

Watson, et al., *Br. J. Cancer*, 1985, 433-435.

Wittwer, C.T. et al., "The LightCycler™: A Microvolume Multisample Fluorimeter with Rapid Temperature Control", *BioTechniques*, vol. 22 (1), Jan. 1997, 176-181.

\* cited by examiner

1

INSTRUMENT FOR MONITORING POLYMERASE CHAIN REACTION OF DNA

CROSS-REFERENCE TO RELATED APPLICATIONS

The present application is a continuation of U.S. patent application Ser. No. 11/804,151, filed May 17, 2007, which is a continuation of U.S. patent application Ser. No. 11/333,483, filed Jan. 17, 2006, now U.S. Pat. No. 8,557,566, which in-turn is a continuation of U.S. patent application Ser. No. 10/216,620, filed Aug. 9, 2002, now U.S. Pat. No. 7,008,789 B2, which in-turn is a continuation of U.S. patent application Ser. No. 09/700,536, filed Nov. 29, 2001, now U.S. Pat. No. 6,818,437 B1, which in-turn is a National Phase Application Under 35 U.S.C. §371 of PCT International Application No. PCT/US99/11088, filed on May 17, 1999, which claims priority benefits from U.S. Provisional Patent Application No. 60/085,765, filed May 16, 1998, and from U.S. Provisional Patent Application No. 60/092,784, filed Jul. 14, 1998, all of which are hereby incorporated herein in their entireties by reference.

BACKGROUND

Polymerase chain reaction (PCR) is a process for amplifying or multiplying quantities of double-stranded deoxyribonucleic acid (DNA). In a PCR apparatus, a thermal cycler block has one or more wells for holding vials containing a suspension of ingredients for a reaction to produce more DNA starting with "seed" samples of the DNA. The starting ingredients in an aqueous suspension, in addition to the a seed sample, include selected DNA primer strands, DNA elements, enzymes and other chemicals. The temperature of the block is cycled between a lower temperature extension phase of the PCR reaction at about 60° C., which is the phase where all of the DNA strands have recombined into double strands, and a high temperature denaturing phase at about 95° C., during which the DNA is denatured or split into single strands. Such a temperature program essentially doubles the DNA in each cycle, thus providing a method for replicating significant amounts of the DNA from a small starting quantity. The PCR process is taught, for example, in U.S. Pat. No. 4,683,202.

Quantitative measurements have been made on the DNA production during the PCR process, to provide measures of the starting amount and the amount produced. Measurements and computation techniques are taught in U.S. Pat. No. 5,766,889 (Atwood), as well as in an article "Kinetic PCR Analysis: Real-time Monitoring of DNA Amplification Reactions" by Russel Higuchi, et al., Bio/Technology vol. 11, pp. 1026-1030 (September 1993), and an article "Product Differentiation by Analysis of DNA Melting Curves during the Polymerase Chain Reaction" by Kirk M. Ririe, et al., Analytical Biochemistry vol. 245, pp. 154-160 (1997).

Prior measuring techniques have utilized microvolume fluorometers (spectrofluorometers) and a simple arrangement of a video camera with illumination lamps. Such apparatus utilize dyes that fluoresce in the presence of double-stranded DNA. These techniques and instruments are not particularly adapted to PCR apparatus for routine monitoring of the reaction. There also is a need for greater precision during the monitoring and measurements. Previous instruments that allow real time acquisition and analysis of PCR data have been very basic devices without the required dynamic range, do not have built-in calibration means, do not allow operation with sample well caps, or are very expensive.

An object of the present invention is to provide a novel optical instrument for quantitative monitoring of DNA replication in a PCR apparatus. Other objects are to provide such an instrument with improved dynamic range, automatic selection of exposure time to extend dynamic range, automatic adjustment for drift, simplified operation, relatively low cost, and easy changing of optics to accommodate different fluorescent dyes.

SUMMARY

The foregoing and other objects are achieved, at least in part, by an optical instrument as described herein for monitoring polymerase chain reaction replication of DNA. The replication is in a reaction apparatus that includes a thermal cycler block for holding at least one vial containing a suspension of ingredients for the reaction. The ingredients include a fluorescent dye that fluoresces proportionately in presence of DNA.

The instrument includes a light source, means for directing light beams, a light detector, and means for processing data signals. The light source emits a source beam having at least a primary excitation frequency that causes the dye to fluoresce at an emission frequency. A first means is disposed to be receptive of the source beam to effect an excitation beam having the excitation frequency. A primary focusing means is disposed to focus the excitation beam into each suspension such that the primary dye emits an emission beam having the emission frequency and an intensity representative of concentration of DNA in each suspension. The focusing means is receptive of and passes the emission beam. A second means is disposed to be receptive of the emission beam from the focusing means so as to further pass the emission beam at the emission frequency to another focusing means that focuses the emission beam onto a detector. The detector generates primary data signals representative of the emission beam and thereby a corresponding concentration of DNA in each vial. A processor is receptive of the primary data signals for computing and displaying the concentration of DNA.

In a preferred embodiment, the first means and the second means together comprise a beam splitter that is receptive of the source beam to effect the excitation beam, and receptive of the emission beam to pass the emission beam to the detector. The block is configured to hold a plurality of vials, and the focusing means comprises a corresponding plurality of vial lenses each disposed over a vial such that the emission beam comprises individual beams each associated with a vial. The focusing means may further comprise a field lens such as a Fresnel lens disposed cooperatively with the vial lenses to effect focusing of the excitation beam into each suspension, and to pass the individual beams to the second means (beam splitter). The detector preferably comprises an array of photoreceptors receptive of the individual beams to generate corresponding data signals such that the processing means computes concentration of DNA in each vial.

The instrument should also include an excitation filter between the light source and the beam splitter, and an emission filter between the beam splitter and the detector. The splitter and filters are associated with a selected primary dye in the suspension. In a further embodiment, a filter module contains the splitter and filters, and the module is removable from the housing for replacement with another module associated with another selected primary dye.

For a reference, a fluorescent reference member emits reference light in response to the excitation beam. The reference is disposed to be receptive of a portion of the excitation beam from the first means. A portion of the reference light is passed by the second means as a reference beam to the detector, so as to generate reference signals for utilization in the computing of the concentration of DNA. Preferably the reference member comprises a plurality of reference emitters, each emitting a reference beam of different intensity response to the excitation beam, to allow selection by the processor of a reference set having the highest data signals that are less than a predetermined maximum that is less than the saturation limit.

The detector is operatively connected to the processing means for the detector to integrate emission beam input over a preselected exposure time for generating each set of data signals, and the processing means or the detector or a combination thereof have a saturation limit for the data signals. In a further aspect of the invention, the processing means comprises adjustment means for automatically effecting adjustments in exposure time to maintain the primary data within a predetermined operating range for maintaining corresponding data signals less than the saturation limit, and means for correcting the primary data in proportion to the adjustments in exposure time. Preferably, the processor computes photoreceptor data from the data signals for each photoreceptor, and the adjustment means ascertains highest photoreceptor data, determines whether the highest photoreceptor data are less than, within or higher than the predetermined operating range and, based on such determination, the exposure time is increased, retained or reduced so as to effect a subsequent exposure time for maintaining subsequent photoreceptor data within the predetermined operating range.

DETAILED DESCRIPTION

An optical instrument A of the invention is utilized with or incorporated into a reaction apparatus B that replicates ("amplifies") selected portions of DNA by polymerase chain reaction ("PCR"). The reaction apparatus is conventional and should function without interference from the instrument which monitors the amount of DNA in real time during replication. Suitable reaction apparatus are described in U.S. Pat. Nos. 5,475,610 and 5,656,493.

Figure 1:
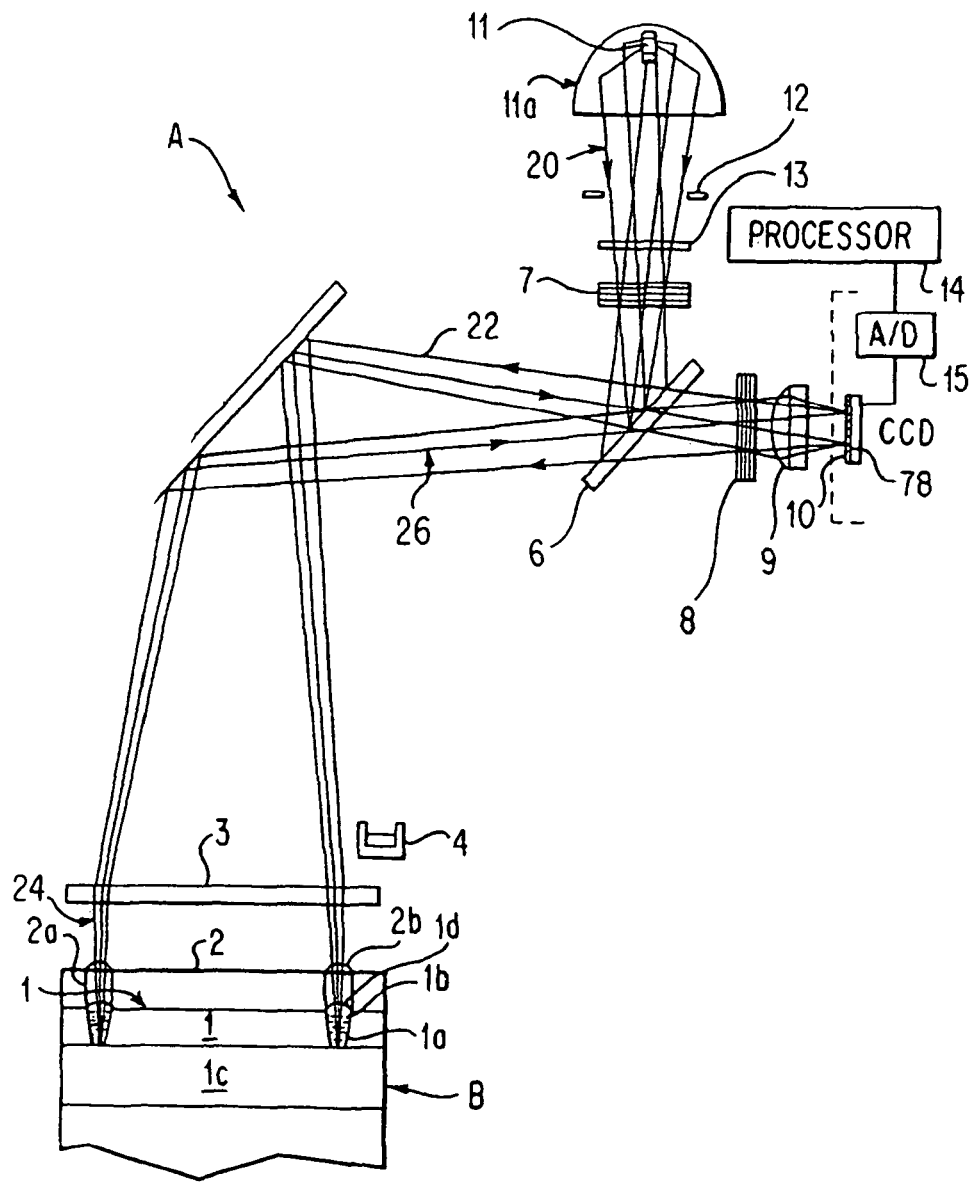
FIG. 1 is a schematic of an optical train for an optical instrument according to the invention, associated with a polymerase chain reaction (PCR) reaction apparatus.

The reaction apparatus (FIG. 1) is conventional and has two main components, namely a thermal cycler block 1 with wells 1a for holding at least one vial 1b containing a suspension of ingredients for the reaction, and a thermal cycle controller 1c for cycling the temperature of the block through a specified temperature program. The starting ingredients of the aqueous suspension of sample materials include a "seed" sample of DNA, selected DNA primer strands, DNA elements, enzymes and other chemicals. The block, typically aluminum, is heated and cooled in a prescribed cycle by electrical means, liquid or air coolant, or a combination of these, or other means to achieve the cycling. The suspensions in the vials are thereby cycled between two temperature phases so as to effect the polymerase chain reaction. These phases are a lower temperature extension phase of the PCR reaction at about 60° C., which is the phase where all of the DNA strands have recombined into double strands, and a high temperature denaturing phase at about 95° C., during which the DNA is denatured or split into single strands.

For the present purpose the sample also contains a fluorescent dye that fluoresces proportionately and more strongly in the presence of double stranded DNA to which the dye binds, for example SYBR Green dye (available from Molecular Probes, Inc., Eugene, Oreg.) that fluoresces in the presence of double stranded DNA. Another type of fluorescent dye labeled "probes", which are DNA-like structures with complimentary sequences to selected DNA strand portions, may also be used. Other dyes that have similar characteristics may be utilized. As used herein and in the claims, the term "marker dye" refers to the type that binds to double stranded DNA, or to the probe type, or to any other type of dye that attaches to DNA so as to fluoresce in proportion to the quantity of DNA. Samples may also contain an additional, passive dye (independent of the DNA) to serve as a reference as described below. Under incidence of light having a correct excitation frequency, generally a dye fluoresces to emit light at an emission frequency that is lower than that of the excitation light.

The vials typically are formed conically in a plastic unitary tray containing a plurality of vials, for example 96 in an array of 12 by 8. The tray preferably is removable from the block for preparations. A plastic unitary cover with caps 1d for the vials may rest or attach over the vials to prevent contamination and evaporation loss. Other means may be used for this function, such as oil on the sample surface, in which case caps are not needed. If used, the caps are transparent to light utilized in the instrument, and may be convex facing upwardly.

The monitoring instrument is mounted over the block containing the vials. The instrument is removable or swings away for access to the vials. In the bottom of the instrument, a platen 2 rests over the vial caps or, if none, directly over the vials. The platen, advantageously aluminum, has an array of holes 2a therethrough aligned with the vials, each hole having a diameter about the same as the vial top diameter. If there are caps, the platen should have its temperature maintained by a film heater or other means for heating the platen sufficiently to prevent condensation under the caps without interfering with DNA replication in the vials, for example holding the platen at slightly higher temperature than the highest sample temperature that the thermal cycler reaches.

Above each of the vials is a lens 2b positioned for its focal point to be approximately centered in the suspension in the vial. Above these lenses is a field lens 3 to provide a telecentric optical system. Advantageously the field lens is an aspherically corrected Fresnel lens for minimal distortion. A neutral density pattern (not shown) to correct nonuniformities in illumination and imaging may be mounted on or in proximity to the field lens, for example to attenuate light in the center of the image field. A folding optical mirror is optionally mounted at 45° for convenient packaging. This may be omitted, or other such folding optics may be used. Also the field lens, and/or the vial lenses, each may be comprised of two or more lenses that effect the required focusing, the word "lens" herein including such multiplicities.

A light source 11 for a source beam 20 of light is provided, for example a 100 watt halogen lamp. Preferably this is mounted at a focal distance of an ellipsoid reflector 11a which produces a relatively uniform pattern over the desired area. Also, advantageously, the reflector should be dichroic, i.e. substantially reflecting visible light and transmitting infrared light, to restrict infrared from the other optical components and from overheating the instrument. This is further aided by a heat reflecting mirror 13 in the optical path. A mechanical or electronic shutter 12 allows blockage of the light source for obtaining dark data. The type of light source is not critical, and other types may be used such as a projection lamp or a laser, with appropriate optical elements.

A beam splitter 6 is disposed to receive the source beam 20. In the present embodiment this is a dichroic reflector such that, positioned at 45°, it reflects light having an excitation frequency that causes the marker dye to fluoresce at an emission frequency, and passes light having the emission frequency. Such a conventional optical device typically utilizes optical interference layers to provide the specific frequency response.

The beam splitter is positioned to reflect the source beam to the folding mirror. The source beam is reflected from the splitter as a excitation beam 22 having substantially the excitation frequency. The excitation beam is focused by the field lens 3 and then as separated beams 24 by the vial (well) lenses 2b into the center of the vials. The marker dye is thereby caused to emit light at the emission frequency. This light is passed upwardly as an emission beam in the form of individual beams 26 that are reflected from the folding mirror 5 to the beam splitter 6 which passes the emission beam through to a detector 10.

Together the vial lenses 2b and the field lens 3 constitute a primary focusing means for is focusing both the excitation beam and the emission beam. In an alternative aspect, the field lens may be omitted so that the focusing means consists only of the vial lenses 2b. Alternatively, the vial lenses may be omitted so that the focusing means consists only of an objective lens in the field lens position to focus the individual emission beams on the detector.

Also, alternatively, the beam splitter 6 may pass the source beam as an excitation beam and reflect the emission beam, with appropriate rearrangement of the lamp and the detector. Moreover, other angles than 45° could be used if more suitable for the beam splitter, such as a more perpendicular reflection and pass through. More broadly, the beam splitter splits the optical paths for the excitation beam and the emission beam, and other variations that achieve this may be suitable. It is desirable to minimize source light reaching the detector, which the dichroic device helps achieve. A non-dichroic beam splitter may be used but would be less efficient as significant source light may reach the detector, or may be reflected or transmitted in the wrong direction and lost.

To further filter the source light, an excitation filter 7 is disposed between the light source 11 and the beam splitter 6. This passes light having the excitation frequency and substantially blocks light having the emission frequency. Similarly, an emission filter 8 is disposed between the beam splitter and the detector, in this case between the splitter and a detector lens 9 in front of the detector. This filter passes light having the emission frequency and substantially blocks light having the excitation frequency. Although a detector lens is preferred, a focusing reflector may be substituted for the detector lens. Such an emission focusing means (detector lens or reflector) may be located after (as shown) or before the beam splitter and on either side of the emission filter, and alternatively may be integrated into the primary focusing means. For example, the field lens may be an objective lens that focuses the emission beam onto the detector.

Suitable filters are conventional optical bandpass filters utilizing optical interference films, each having a bandpass at a frequency optimum either for excitation of the fluorescent dye or its emission. Each filter should have very high attenuation for the other (non-bandpass) frequency, in order to prevent "ghost" images from reflected and stray light. For SYBR Green dye, for example, the excitation filter bandpass should center around 485 nm wavelength, and the emission filter bandpass should center around 555 nm. The beam splitter should transition from reflection to transmission between these two, e.g. about 510 nm, so that light less than this wavelength is reflected and higher wavelength light is passed through.

More broadly, the excitation filter and the beam splitter together constitute a first means disposed to be receptive of the source beam to effect an excitation beam having the excitation frequency, and the emission filter and the beam splitter together constitute a second means disposed to be receptive of the emission beam from the focusing means so as to pass the emission beam at the emission frequency to the detector. Also, as mentioned above, the beam splitter alternatively may pass the source beam as an excitation beam and reflect the emission beam to the detector. In another aspect, the filters may be omitted, and the first means is represented by the beam splitter effecting the exitation beam from the source beam, and the second means is represented by the beam splitter passing the emission beam to the detector.

In another arrangement, the beam splitter may be omitted, and the first means may constitute an excitation filter for the excitation frequency, the second means may constitute an emission filter for the emission frequency, with the light source and the detector being side by side so that the excitation and emission beams are on slightly different optical paths angularly. The source and detector need not actually be side by side with one or more folding mirrors. Thus any such arrangement for achieving the effects described herein should be deemed equivalent. However, use of the beam splitter is preferred so that the excitation and emission beams through the field lens will have the same optical path.

Figure 2:
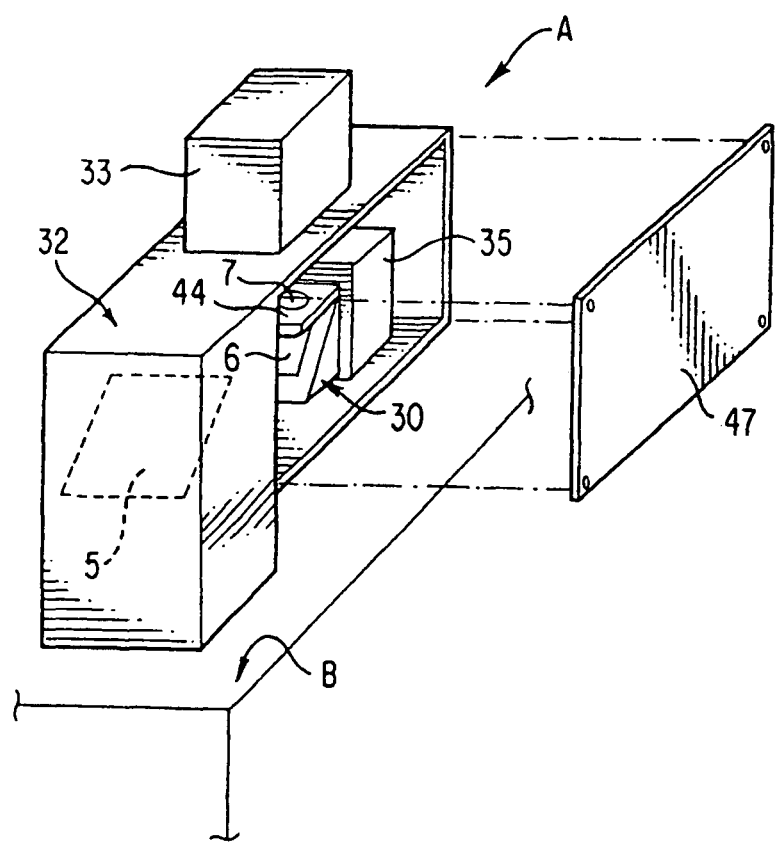
FIG. 2 is a perspective of the instrument of FIG. 1 with a side panel removed.

Advantageously the beam splitter 6, the excitation filter 7 and the emission filter 8 are affixed in a module 30 (FIG. 2) that is associated with a selected primary dye for the suspension. The module is removable from the housing 32 of the instrument A for replacement with another module containing different beam splitter and filters associated with another selected primary dye. The instrument includes a lamp subhousing 33 and a camera subhousing 35.

Figure 3:
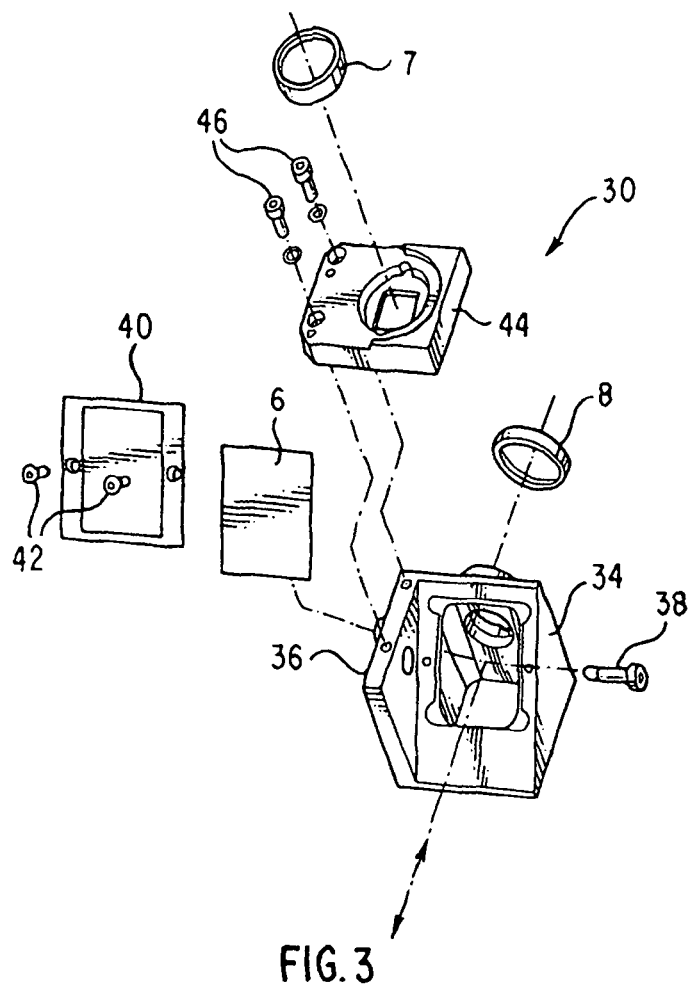
FIG. 3 is an exploded perspective of a module shown in FIG. 2.

In an example (FIG. 3), each module includes a mounting block 34 with a flange 36 that is affixable to the housing with a single screw 38. The beam splitter 6 is held at 45° in the block with a frame 40 and screws 42. The emission filter 8 mounts (e.g. with glue) into the block. The excitation filter 7 mounts similarly into a mounting member 44 that is held by screws 46 to the block. With the module in place, the instrument is closed up with a side plate 47 that is screwed on. Positioning pins (not shown) ensure repeatable alignment. The replacement module may have the same mounting block and associated components, with the beam splitter and filters replaced.

The detector lens 9 (FIG. 1) is cooperative with the vial lenses 2b and the field lens 3 to focus the individual beams on the detector 10. The lens should be large aperture, low distortion and minimum vignetting.

The detector preferably is an array detector, for example a charge injection device (CID) or, preferably, a charge coupled device (CCD). A conventional video camera containing a CCD detector, the detector lens and associated electronics for the detector should be suitable, such as an Electrim model 1000L which has 751 active pixels horizontal and 242 (non-interlaced) active pixels vertical. This camera includes a circuit board that directly interfaces to a computer ISA bus. No framegrabber circuitry is required with this camera. Essentially any other digital imaging device or subsystem may be used or adapted that is capable of taking still or freeze-frame images for post processing in a computer.

A detector with a multiplicity of photoreceptors (pixels) 78 is preferable if there are a plurality of vials, to provide separate monitoring of each. Alternatively a scanning device may be used with a single photodetector, for example by scanning the folding mirror and using a small aperture to the detector. Also, a simple device such as a photomultipier may be used if there is only one vial. A CCD receives light for a selected integration period and, after analog/digital conversion, reads out digital signal data at a level accumulated in this period. The integration is effectively controlled by an electronic shutter, and a frame transfer circuit is desirable. Signal data are generated for each pixel, including those receiving the individual beams of emitted light from the vials.

The instrument preferably includes a fluorescent reference member 4 that emits reference light in response to the excitation beam. Advantageously the reference member is formed of a plurality of reference emitters, e.g. 6, each emitting a reference beam of different intensity in response to the excitation beam. The range of these intensities should approximate the range of intensities expected from the marker dye in the vials; for example each segment may be separated in brightness by about a factor of 2.5. The reference member is disposed to receive a portion of the excitation beam from the beam splitter. A good location is adjacent to the field lens, so that the optical paths associated with the member approximate those of the vials. Most of the reference light passes back through the beam splitter as a reference beam to the detector. The detector pixels receive the emission beam to generate reference signals for utilization along with the data signals in the computing of the concentration of DNA.

Figure 4:
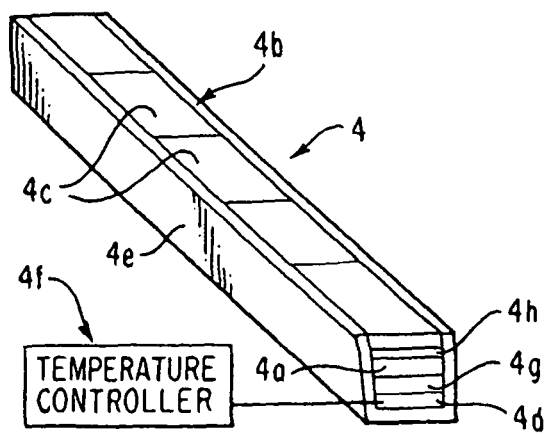
FIG. 4 is a perspective of a reference member in the optical train of FIG. 1.

Advantageously the reference member 4 (FIG. 4) comprises a plastic fluorescent strip 4a and a neutral density filter 4b mounted over the fluorescent strip, optionally with an air space 4h between, such that a portion of the excitation beam and the reference beam are attenuated by the neutral density filter. The neutral density filter has a series of densities 4c to effect the plurality of reference emitters (segments) each emitting a reference beam of different intensity. A heating strip 4d and an aluminum strip 4g to smooth the heating are mounted in a trough 4e on the bottom thereof, and the fluorescent strip is mounted on the aluminum strip over the heating strip. To prevent heat loss, this assembly preferably is covered by a transparent plexiglass window (not shown, so as to display the varying density filter). To help maintain constant fluorescence, the heating strip is controlled to maintain the fluorescent strip at a constant temperature against the thermal cycles of the cycler block and other effects. This is done because most fluorescent materials change in fluorescence inversely with temperature.

The computer processor 14 (FIG. 1) may be a conventional PC. The computer programming is conventional such as with "C". Adaptations of the programming for the present invention will be readily recognized and achieved by those skilled in the art. The processor selectively processes signals from pixels receiving light from the vials and the reference emitters, ignoring surrounding light. The programming therefore advantageously includes masking to define the pixel regions of interest (ROI), e.g. as disclosed in copending provisional patent application Ser. No. 60/092,785 filed Jul. 14, 1998 of the present assignee. Mechanical alignment of the optics may be necessary to cooperatively focus the beams into the programmed regions of interest. The analog data signals are fed to the processor through an analog/digital (A/D) device 15 which, for the present purpose, is considered to be part of the processor. A saturation level is proscribed by either the detector or the A/D or, preferably, the CCD dynamic range is matched to the A/D dynamic range. A suitable range is 8 bits of precision (256 levels), and the CCD amplifier offset is set so that the dark signal output of the CCD (with the shutter 12 closed) is within the A/D range. The processor instructs the detector with selected exposure time to maintain the output within the dynamic range.

Figure 5:
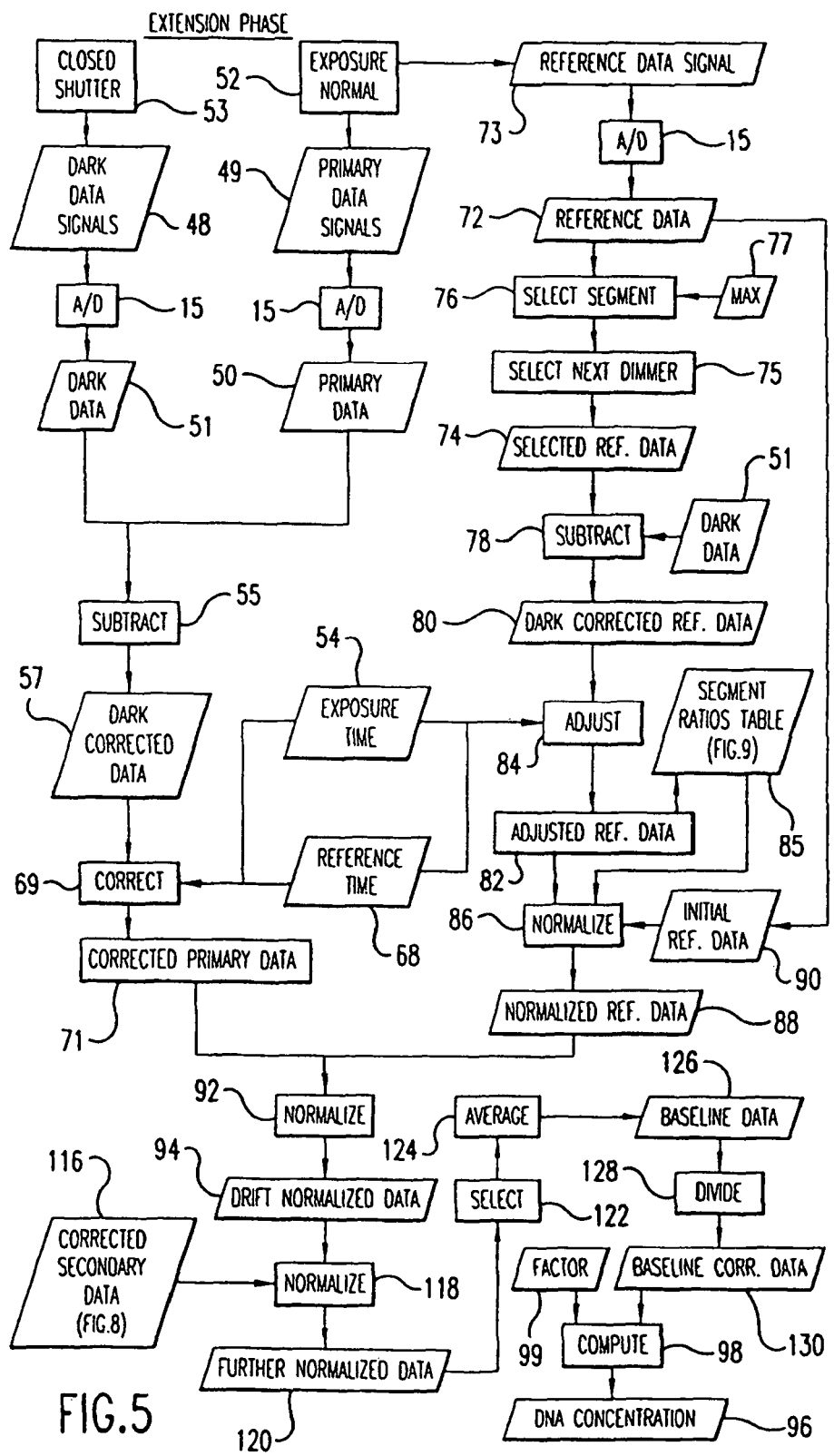
FIG. 5 is a flow chart for computing DNA concentration from data obtained with the instrument of FIG. 1.

In a typical operation, fluorescence data are taken from the plurality of vials (e.g. 96 regions of interest) and from the reference emitter segments, for each cycle in a DNA reaction replication sequence of thermal cycles, typically 40 to 50. Two data sets are taken (FIG. 5) for each thermal cycle during the extension phase of the PCR reaction at about 60° C., which is the phase where all of the DNA strands have recombined into double strands. One set is normal primary data 50 (along with reference data described below) and the other is dark signal data 51 with the mechanical shutter closed. Both digital data sets 50, 51 are converted by the A/D 15 from respective analog data signals 48, 49 from the detector. The dark are subtracted 55 from the normal, to yield dark-corrected data 57. In a simple procedure, the subtraction is pixel by pixel. Alternatively, total dark for each region of interest are subtracted from corresponding total fluorescence data. In another alternative, in order to increase effective dynamic range, it is advantageous to collect multiple exposures during each exposure period, e.g. 4 or 8 exposures. This is done by collecting multiple normal exposures and dark signal data for each pixel, subtracting each respective dark image from the normal data, then adding the subtracted data together to yield the primary data. This improves the statistical validity of the image data and increases its effective dynamic range.

Figure 6:
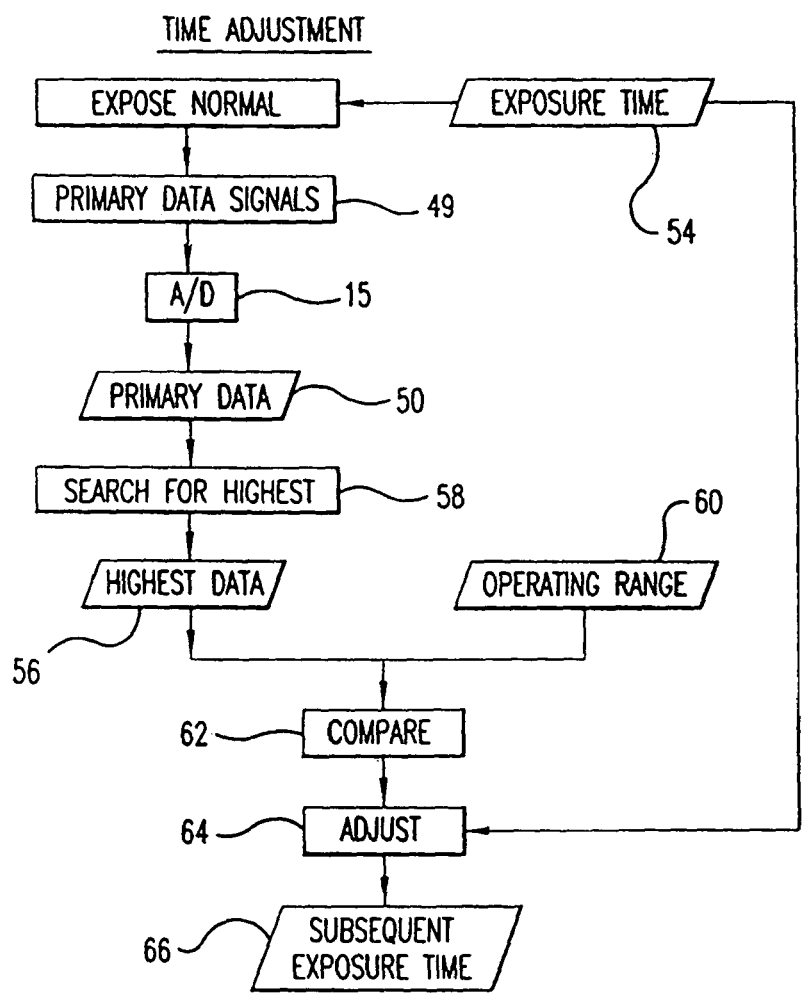
FIG. 6 is a flow chart for determining exposure time for data acquisition in operation of the instrument of FIG. 1 and for computations in the flow chart of FIG. 5.

Data are taken simultaneously from the reference strip which has, for example, 6 segments together with the 96 vials for a total of 102 regions of interest. Preferably the processing means provides for automatic adjustment of the exposure time to maintain the data signals within a predetermined operating range that is less than the saturation limit during the DNA replication sequence, for example 35% to 70% of saturation. Computations for DNA concentration include corrections in proportion to adjustments in exposure time (FIG. 6). Signal data 50, 51 from each exposure 52, 53 are obtained during a previously determined exposure time 54 by totaling the pixel counts within each region of interest (ROI).

Figure 7:
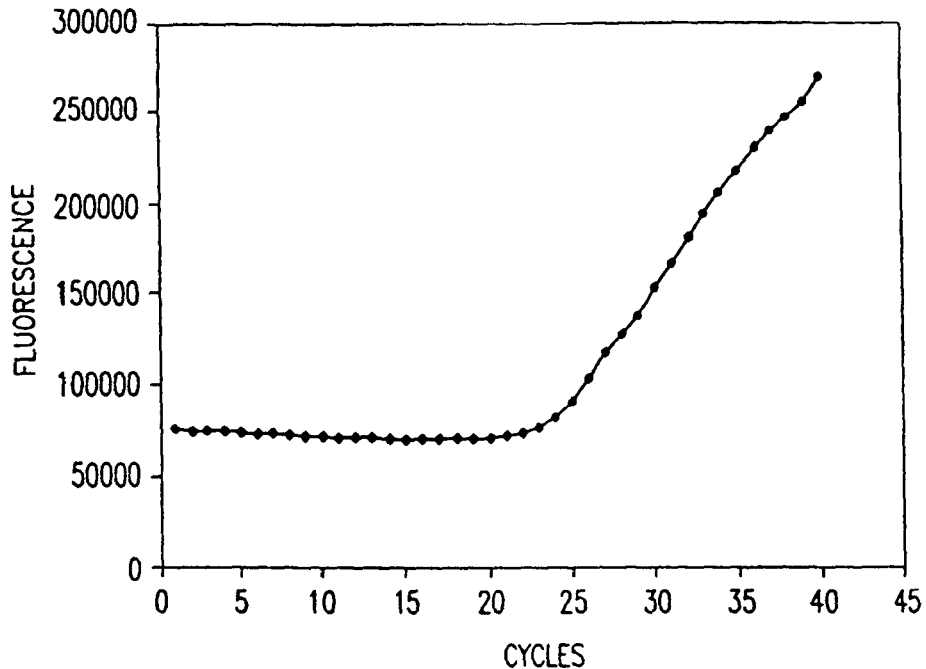
FIG. 7 is a graph of extension phase data of fluorescence vs. cycles from operation of the instrument of FIG. 1 with a PCR apparatus.

To provide the time adjustments, the highest signal data 56, which is data from one or more highest pixel readings, such as the three highest-reading contiguous pixels, is searched out 58 from the corresponding data signals 50. From a comparison 62 it is determined whether the highest signal data are less than, within or higher than the selected operating range 60. Based on such determination, the exposure time is adjusted 64, i.e. increased, retained or reduced, to obtain the subsequent exposure time 66. A reference time 68 (FIG. 5) also is selected which may be, for example, an initial time or a fixed standard time such as 1024 ms. The dark-corrected data 57 is time-corrected 69 to yield corrected primary data 71, dividing by ratio of actual exposure time to the reference time. The first several cycles may be out of range, and thereafter a useful fluorescence curve should be obtained (FIG. 7).

For the reference emitter, from the pixels receiving light from the reference strip 4 (FIGS. 1 and 4) reference data signals 73 are generated and converted by the A/D 15 to reference data 72. Selected reference data 74 from a specific reference segment 4c (FIG. 4) are selected 76 as that data having the highest signal strength that is less than a predetermined maximum 77 that, in turn, is less than the saturation limit, e.g. 70%. A next dimmer segment is also selected 75, and the selected reference data 74 include the data from that segment. The dark data 51 are subtracted 78 from the reference data 74, and the dark-corrected data 80 are adjusted 84 for exposure time 54 to yield adjusted reference data 82.

Figure 9:
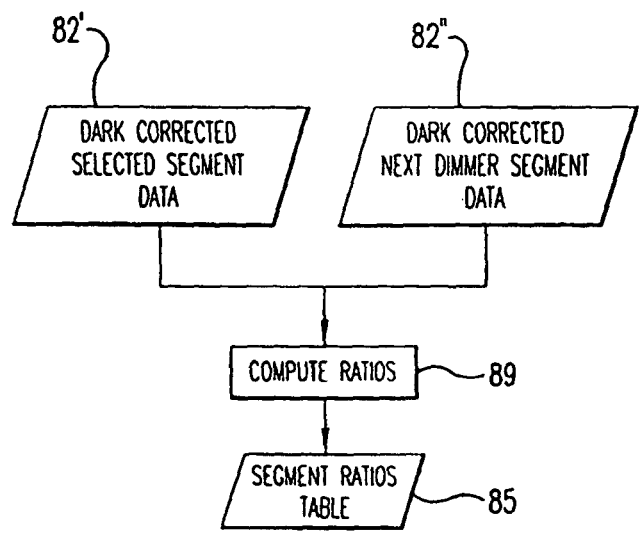
FIG. 9 is a flow chart for computing ratios between the plurality of reference emitter segments of the reference member of FIG. 4.

The data 82 includes dark corrected data 82' for the highest segment and dark corrected data 82" for the next dimmer segment (FIG. 9). The ratios of brightness between each segment are computed 89 and built up over the course of data collection. Each time data is collected, the ratio between the highest and next dimmer segment is calculated. As different optimum segments are selected on succeeding data collections, a table of ratios 85 is assembled. Alternatively, these rations may be collected and calculated in advance.

This adjusted reference data 82' (from data 82, FIG. 5) are utilized for computing normalized reference data 88 which are normalized 86 in real time as a ratio to reference data 90 from an initial or other selected previous cycle in the DNA replication (PCR) sequence by working back with the ratios 85. The normalized reference data are utilized on the corrected primary data 71 in a normalization computation 92 to provide drift normalized primary data 94 by dividing the primary data by the normalized reference data. This corrects for instrument drift during the monitoring. DNA concentration 96 may then be computed 98 from a stored calibration factors 99, determined by running standard known DNA concentrations to determine the slope and intercept of a line relating starting concentration to the starting cycle of the growth curve (FIG. 7) as taught in the aforementioned article by Higuchi and U.S. Pat. No. 5,766,889. (Further normalization 118, 120 and baseline correction 122-130 are discussed below.)

Extension phase data for a typical PCR sequence would look like FIG. 7, plotted for each PCR cycle. If desired, the data may be corrected for dye bleaching or other sample chemical effects by normalizing to sample vials containing samples with the same dye and with DNA amplification prevented chemically.

The sample additionally may contain one or more types of dye molecules that serve as a "passive" reference having some fluorescence in the same wavelength range as the DNA binding dye. This reference dye is made up, for example, of a nucleic acid sequence labeled with Rhodamine and Fluorescein dye derivatives. A suitable reference is Rox dye from Perkin-Elmer Applied Biosystems. These passive dye molecules do not take part in the PCR reaction, so that their fluorescence is substantially without influence from DNA and remains constant during the reaction. This fluorescence can be used to normalize the fluorescence from the DNA binding dye with a standard concentration of passive dye included in the ingredients of at least one vial, preferably in every vial.

The source beam includes a secondary excitation frequency that causes the passive dye to fluoresce at a secondary frequency and thereby emit a secondary beam directed to the detector to generate corresponding secondary data signals. The processor is receptive of the secondary data signals for computing secondary data representative of standard concentration. These data are used to normalize the primary data, so that the concentration of DNA is normalized to the standard concentration of passive dye after correcting computations of concentration of DNA in proportion to adjustments in exposure time, and in conjunction with the normalization for drift. Advantageously, and in the present example, the secondary excitation frequency is identical to the primary excitation frequency, and the passive dye fluoresces such that the emitted secondary beam is substantially at the emission frequency. The primary data signals are generated during each extension phase of cycling of the thermal cycler block when DNA is recombined and correspondingly primary dye emission is maximized. The secondary data signals are generated during each denature phase of cycling of the thermal cycler block when DNA is denatured and correspondingly primary dye emission is minimized. Thus data signals for the primary phase are substantially representative of DNA concentration, and data signals for the secondary phase are substantially representative of the standard concentration of passive dye.

The dark and normal data are taken for the vial samples and the reference strip, and the dark is subtracted from the normal fluorescence data. This dark and normal data set is taken during the extension phase of the PCR reaction at about 60° C., which is the phase where all of the DNA strands have recombined into double strands. During this phase, the fluorescence from the DNA binding dye is maximized, and the fluorescence from the passive reference molecules is superimposed but much smaller. A separate dark and normal data set is taken during the high temperature (about 95° C.) denaturing phase, during which the DNA is denatured or split into single strands. During this phase, the fluorescence of the DNA binding dye is minimized, and almost non-existent, because the DNA is not double stranded and the fluorescence of the dyes used have a large decrease in fluorescence with increased temperature. Therefore the denaturing phase images substantially contain reference fluorescence from the passive reference molecules. The dark-corrected reference (denaturing) data set, after correction for measured temperature dependence, may be subtracted from the dark-corrected DNA binding dye data set, or may be deemed insignificant for the normal data set.

Alternatively, it may be desirable to image the passive reference dye labeled molecules by taking the additional images, for each PCR cycle, using a separate optical bandpass filter that rejects wavelengths emitted by the DNA binding dye while accepting wavelengths from the passive reference dye. This data would be functionally equivalent to the denature data.

Figure 8:
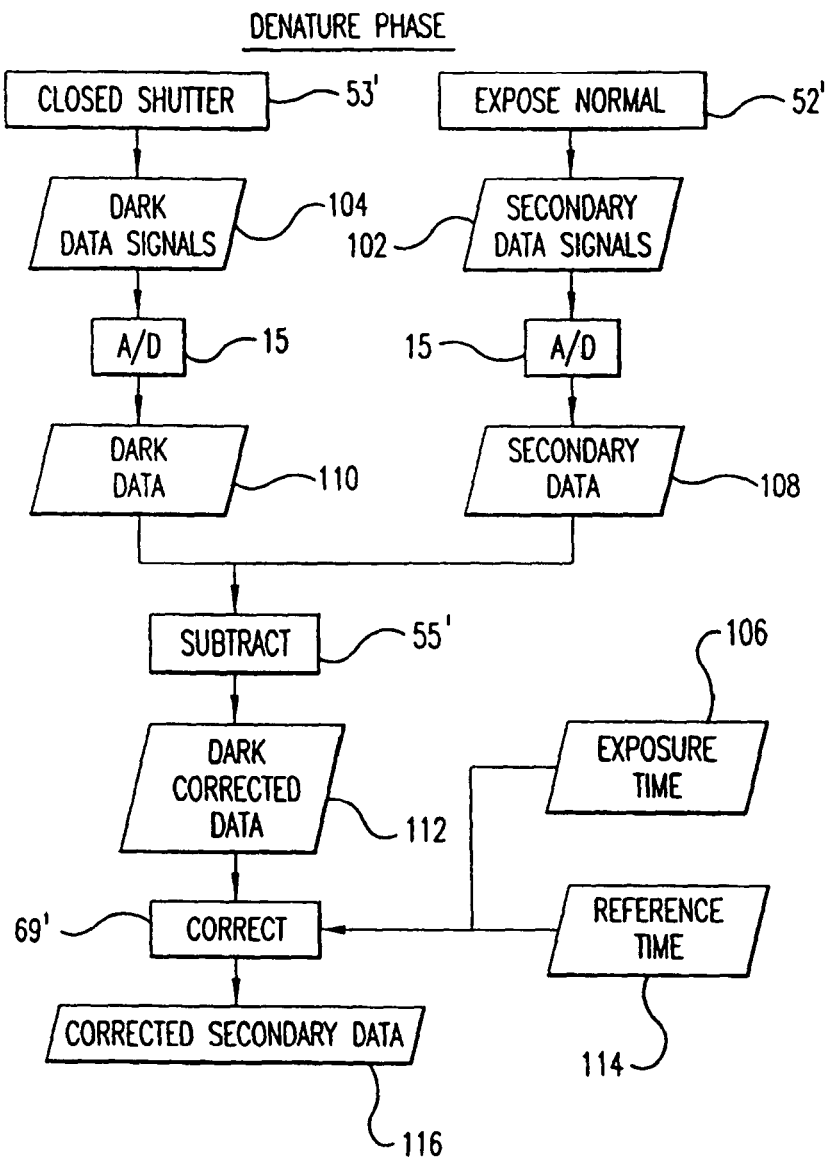
FIG. 8 is a flow chart for computing secondary data for computations in the flow chart of FIG. 5.

Illustrating operation for the denature phase (FIG. 8), respective normal and dark data signals 102, 104 are obtained in the same manner as for the primary data, with normal exposure 52' and closed shutter 53'. Exposure time 106 may be the same as for an adjacent extension phase in the sequence, or determined from a previous denature phase run (as described with respect to FIG. 7), or may be a suitable time predetermined for all denature phases in the sequence. The A/D 15 converts the signals to secondary data 108 and dark data 110. The dark is subtracted 55' from the secondary to yield dark-corrected data 112 which is further corrected 69' with a reference time 114 and the actual exposure time 106 to yield corrected secondary data 116.

The extension cycle, drift normalized primary data 94 then are normalized 118 by dividing by the average of a selected number (e.g. 10) of cycles for the denature phase corrected secondary data 116 to produce further normalized fluorescence data or further normalized data 120, which removes sample well to well non-uniformity effects. Cycle by cycle division may be used in place of an average. Alternatively the secondary data may be applied to the corrected primary data 71 before or after drift normalization. Baseline samples may be selected 122 and averaged 124 to produce baseline data 126. The further normalized data 120 are then divided 128 by the baseline data to yield baseline corrected data 130. These baseline samples are selected so as to be before the PCR growth exceeds the nearly horizontal base line portion of the curve in FIG. 7. Selected baseline cycles may be, for example, cycles 6 through 15. After further normalization 118, the further normalized data 118 are used to compute 98 DNA concentration 96.

The trend (e.g. least squares regression line) of these same baseline samples is subtracted from the normalized extension cycle data, to produce data that has a flat base line at zero. This data set may then be processed using established or other desired PCR methods to calculate the amount of starting copies of DNA. A simple procedure is to extrapolate for the inflection point at the transition from flat to rising. A more sophisticated procedure is described in the aforementioned U.S. Pat. No. 5,766,889.

The data may be used for various purposes, for example quantitative monitoring of the reaction or determination of replicated DNA concentration, or determination of the to starting amount. The instrument also may be used (with or without normalizations and other corrections) simply to display whether replication is taking place during a sequence, or has taken place.

While the invention has been described above in detail with reference to specific embodiments, various changes and modifications which fall within the spirit of the invention and scope of the appended claims will become apparent to those skilled in this art. Therefore, the invention is intended only to be limited by the appended claims or their equivalents.

What is claimed is:

1. An instrument comprising:
an apparatus configured to hold a plurality of spaced-apart reaction regions;
a light source configured to direct an excitation beam toward the apparatus;
a detector configured to receive emission beams from the apparatus;
an excitation beam path disposed from the light source to the apparatus;
an emission beam path disposed from the apparatus to the detector; and
a lens disposed along the excitation beam path and along the emission beam path, the lens configured to direct the excitation beam to more than one of the reaction regions simultaneously.

2. The instrument of claim 1, wherein the light source comprises a laser.

3. The instrument of claim 1, further comprising a dichroic reflector configured to reflect the excitation beam.

4. The instrument of claim 1, wherein the light source is configured to emit at least two excitation beams, each excitation beam characterized by a central wavelength that is different from that of the other excitation beam(s).

5. The instrument of claim 4, further comprising a plurality of dichroic reflectors configured to reflect the at least two excitation beams from the light source.

6. The instrument of claim 1, wherein lens comprises a focusing optic.

7. The instrument of claim 1, wherein the lens is located proximal to the apparatus.

8. The instrument of claim 1, wherein the instrument comprises the plurality of spaced-apart reaction regions and at least some of the reaction regions comprise one or more of a component for DNA replication, a fluorescent dye, or a dye labeled probe.

9. The instrument of claim 1, wherein the instrument comprises the plurality of spaced-apart reaction regions wherein at least two reaction regions each produce an emission beams that simultaneously passes through the lens and onto the detector.

10. The instrument of claim 1, wherein the apparatus comprises a PCR reaction apparatus.

11. The instrument of claim 1, wherein the apparatus comprises a heater to maintain a temperature.

12. An instrument comprising:
an apparatus having a surface configured to hold a plurality of spaced-apart reaction regions;
a light source configured to generate an excitation beam;
a detector configured to detect emission beams from the apparatus;
an excitation beam path disposed from the light source to the surface of the apparatus;
an emission beam path disposed from the surface of the apparatus to the detector; and
a lens disposed along the excitation beam path and the emission beam path, the lens configured to direct the excitation beam to the surface configured to hold a plurality of spaced-apart reaction regions;
wherein said lens is configured to simultaneously illuminate a plurality of spaced-apart reaction regions.

13. The instrument of claim 12, wherein the light source comprises a laser.

14. The instrument of claim 12, further comprising a dichroic reflector configured to reflect the excitation beam.

15. The instrument of claim 12, wherein the light source emits at least two excitation beams, each excitation beam characterized by a central wavelength that is different from that of the other excitation beam(s).

16. The instrument of claim 15, further comprising a plurality of dichroic reflectors configured to reflect light from the light source.

17. The instrument of claim 12, wherein lens comprises a focusing optic.

18. The instrument of claim 12, wherein the apparatus comprises a PCR reaction apparatus.

19. The instrument of claim 12, wherein the apparatus comprises a heater to maintain a temperature.

20. An instrument comprising:
an apparatus having a portion configured to hold a plurality of spaced-apart reaction regions;
a light source configured to direct an excitation beam toward the portion;
a detector configured to receive emission beams from the portion; and
a lens configured to direct the excitation beam to the portion, to illuminate more than one reaction region simultaneously, and to direct emission beams from the portion to the detector to produce data signals.

21. The instrument of claim 20, wherein the light source comprises a laser.

22. The instrument of claim 20, further comprising a dichroic reflector configured to reflect the excitation beam.

23. The instrument of claim 20, wherein the light source emits at least two excitation beams, each excitation beam characterized by a central wavelength that is different from that of the other excitation beam(s).

24. The instrument of claim 23, further comprising a plurality of dichroic reflectors configured to reflect light from the light source.

25. The instrument of claim 20, wherein lens comprises a focusing optic.

26. The instrument of claim 20, wherein the apparatus comprises a PCR reaction apparatus.

27. The instrument of claim 20, wherein the apparatus comprises a heater to maintain a temperature.

* * * * *